United States Patent [19]
Hawkins et al.

[11] Patent Number: 5,674,985
[45] Date of Patent: Oct. 7, 1997

[54] PROCESS FOR PREPARING CERIUM (IV) CATALYST COMPOUNDS

[75] Inventors: Ian Michael Hawkins, Lancashire, United Kingdom; Heiko Heinrich Karl Mauermann, Plainsboro, N.J.

[73] Assignee: Rhone-Poulenc Chemicals Limited, Hertfordshire, United Kingdom

[21] Appl. No.: 477,572

[22] Filed: Jun. 7, 1995

Related U.S. Application Data

[60] Division of Ser. No. 184,197, Jan. 18, 1994, Pat. No. 5,449,387, which is a continuation-in-part of Ser. No. 77,362, Jun. 17, 1993, abandoned.

[30] Foreign Application Priority Data

Jun. 17, 1992 [GB] United Kingdom ............... 9212811
Sep. 23, 1992 [GB] United Kingdom ............... 9220116

[51] Int. Cl.$^6$ ............................. C07F 5/00; C01F 17/00
[52] U.S. Cl. ............................................................ 534/16
[58] Field of Search .................................... 534/15, 16

[56] References Cited

U.S. PATENT DOCUMENTS

| | | | |
|---|---|---|---|
| 3,231,592 | 1/1966 | McCord | 260/414 |
| 4,264,335 | 4/1981 | Bello et al. | 44/68 |
| 4,545,923 | 10/1985 | Gradeff et al. | 252/309 |
| 4,599,201 | 7/1986 | Gradeff et al. | 260/414 |
| 4,647,401 | 3/1987 | Gradeff et al. | 252/309 |
| 4,794,172 | 12/1988 | Kreh | 534/15 |
| 4,886,624 | 12/1989 | Gradeff et al. | 252/308 |
| 4,920,204 | 4/1990 | Gradeff et al. | 534/15 |
| 5,002,747 | 3/1991 | LeLoarer | 423/592 |
| 5,023,070 | 6/1991 | LeLoarer | 423/592 |
| 5,099,006 | 3/1992 | Gradeff et al. | 534/15 |
| 5,132,048 | 7/1992 | Picard-Souefal | 252/313.1 |
| 5,145,605 | 9/1992 | Chane-Ching et al. | 252/313.1 |
| 5,279,789 | 1/1994 | LeLoarer et al. | 423/21.1 |
| 5,449,387 | 9/1995 | Hawkins et al. | 44/364 |

FOREIGN PATENT DOCUMENTS

| | | |
|---|---|---|
| A-0433133 | 6/1991 | European Pat. Off. . |
| A1475971 | 6/1977 | United Kingdom . |

OTHER PUBLICATIONS

Chemical Abstracts CA 119(12):130290 F, 1993.

*Primary Examiner*—John Kight
*Assistant Examiner*—Lara Chapman Kelley
*Attorney, Agent, or Firm*—Burns, Doane, Swecker & Mathis, L.L.P.

[57] ABSTRACT

Novel cerium (IV) oxidic compounds, well suited as catalysts, e.g., for the clean combustion of hydrocarbon fuels and for the "drying" of paint compositions, each Ce(IV) atom of which being coordinated with two anions of an organic oxyacid advantageously having a pKa greater than 1, preferably greater than 2, or a mixture of such oxyacids, and the oxidic oxygen atom or atoms of which being other than those comprising the organic oxyacids; representative such novel cerium (IV) oxidic compounds, whether yellow crystalline solids or yellow liquids, have the formula:

$$(H_2O)_p[CeO(A)_2.(AH)_n.]_m$$

in which the radicals A, which may be the same or different, are each the residue of an organic oxyacid of formula AH, p is an integer ranging from 0 to 5, n ranges from 0 to 2 and m is an integer ranging from 1 to 12.

14 Claims, 7 Drawing Sheets

PROCESS FOR PREPARING CERIUM (IV) CATALYST COMPOUNDS

CROSS-REFERENCE TO PARENT APPLICATION

This application is a divisional of application Ser. No. 08/184,197, filed Jan. 18, 1994, now U.S. Pat. No. 5,449,387 which is a CIP of application Ser. No. 08/077,362, filed Jun. 17, 1993 now abandoned.

BACKGROUND OF THE INVENTION

1. Field of the Invention

The present invention relates to novel cerium (IV) oxidic compounds and to the preparation and applications thereof, and, more especially, to novel cerium (IV) oxidic compounds that are soluble in organic solvents, notably the hydrocarbons, or are convertible into cerium (IV) oxidic compounds that are soluble in such hydrocarbons.

2. Description of the Prior Art

It is known to this art that cerium serves as a catalyst for numerous applications. In particular, it is useful for catalyzing the crosslinking of film-forming compositions which dry via atmospheric oxidation, e.g., paint films, and it has been described as a catalyst for the oxidation of combustion residues and exhaust gases of hydrocarbon fuels, e.g., diesel fuels, as described in U.S. Pat. No. 4,522,631.

For these various applications, it is important to produce cerium compounds in the cerium (IV) valence state, which is often the catalytically active state. Such cerium (IV) compounds are soluble in organic solvents, stable, and can be stored at high cerium concentrations.

U.S. Pat. No. 4,599,201 to Gradeff et al, and counterpart EP-A-0,093,627, both assigned to the assignee hereof, describe the synthesis of ceric carboxylates which are soluble in organic solvents, from a solution of a cerium (III) compound which is oxidized in an organic medium. Although this process presents several advantages, it also presents the following disadvantages:

(1) the final products obtained are ill-defined and in particular comprise a mixture of cerium (III) and cerium (IV) values in which the proportion of Ce(IV) is not above 75%;

(2) the solutions obtained are extremely viscous and their long term stability is doubtful;

(3) hydrogen peroxide must be used; and (4) a fraction of the cerium values is lost, in the form of water-soluble byproducts.

SUMMARY OF THE INVENTION

Accordingly, a major object of the present invention is the provision of novel cerium (IV) oxidic compounds that are improvedly soluble in organic solvents, and which otherwise avoid or conspicuously ameliorate the above disadvantages and drawbacks to date characterizing the state of this art.

Briefly, the present invention features the preparation of novel cerium (IV) oxidic compounds containing, for each Ce(IV) atom, two residues of an organic oxyacid, advantageously at least one of which having a pKa greater than 1, or of a mixture of such acids, and one other oxygen atom bonded to said Ce(IV) atom in addition to the oxygen atoms constituting said organic oxyacid residues (this oxygen atom being referred to as the "oxidic" oxygen atom), comprising reacting, preferably in aqueous solution, a cerium (IV) salt with a salt of said organic oxyacid advantageously having a pKa greater than 1, or with a mixture of salts of organic oxyacids, at least one of which advantageously having a pKa greater than 1.

DETAILED DESCRIPTION OF BEST MODE AND PREFERRED EMBODIMENTS OF THE INVENTION

Figure 1:
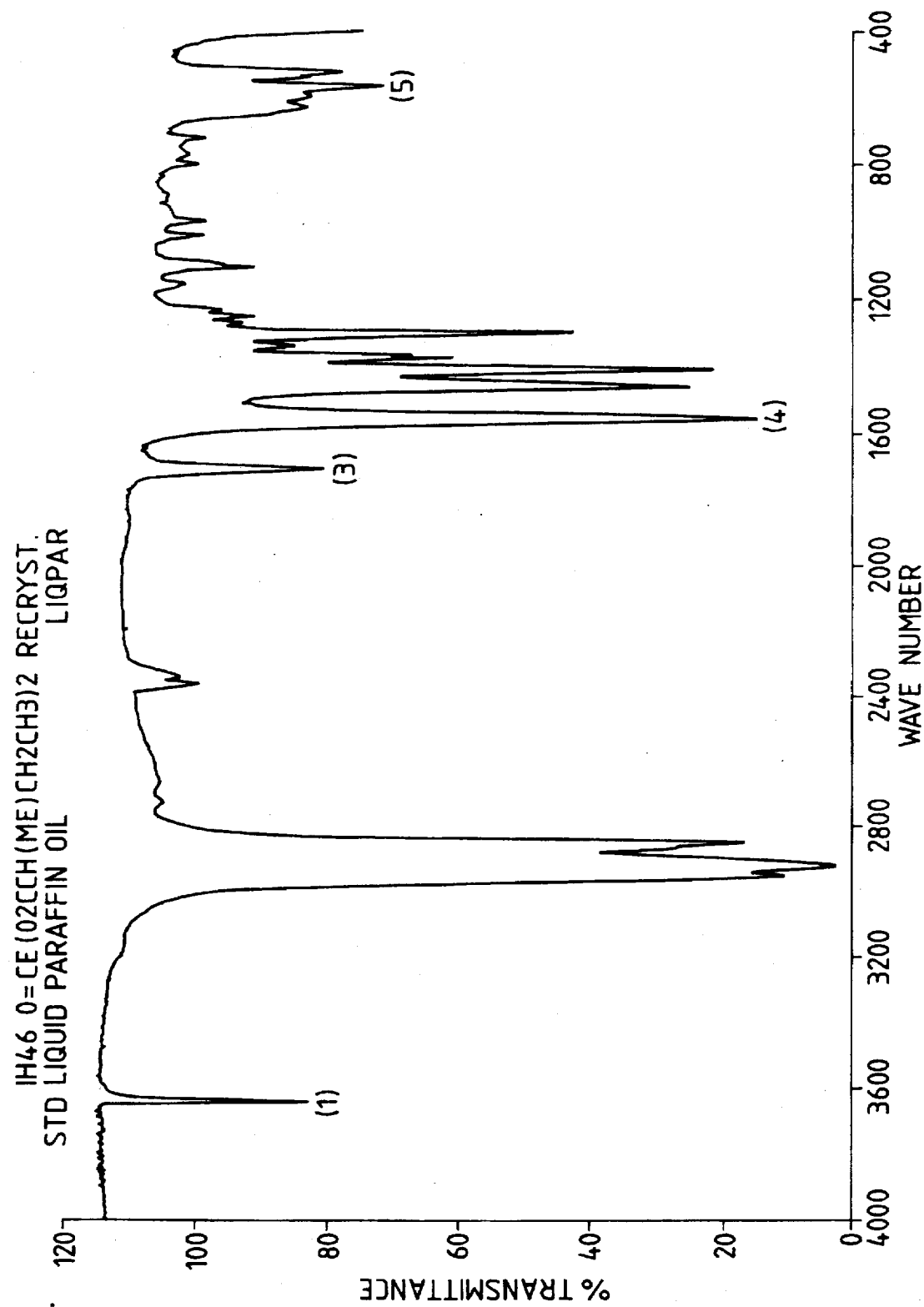
FIGS. 1, 2 and 3 are infrared spectra of the compounds of Examples 2, 4 and 8 according to the present invention.

More particularly according to the present invention, the organic oxyacid is preferably a carboxylic acid, but may also be an organic sulfuric, sulfonic, phosphoric or phosphonic acid having an appropriate pKa. The subject novel cerium (IV) oxidic compounds are storage stable in the pure state and also when dissolved in a hydrocarbon solvent, and the cerium (IV) content thereof is at least 90%, typically at least 95%, and often at least 99% of the total cerium content.

The novel cerium (IV) oxidic compounds are obtained as yellow crystalline solids, or as yellow liquids. They may be represented by the formula:

$$(H_2O)_p[CeO(A)_2 \cdot (AH)_n \cdot ]_m$$

in which the radicals A, which may be the same or different, are each the residue of an organic oxyacid as defined above of formula AH, p is an integer ranging from 0 to 5, n ranges from 0 to 2 and m is an integer ranging from 1 to 12. More particularly, n preferably is 0 or 2, p is 4, and m is 6. The cerium (IV) oxidic compounds containing the organic oxyacid residues in which n is greater than 0 (preferably 2) are liquids which are miscible with organic hydrocarbon solvents. When n is 0, the compounds are crystalline solids which, if not soluble in hydrocarbon solvents, may be solubilized by reacting same with an acid, or a mixture of acids, to provide a product in which n is greater than 0, e.g., is 2.

X-ray analysis of the novel compounds, when crystallized, have shown that at least in certain instances the cerium atoms are arranged at the apexes of an octahedron with each of the eight faces capped by a triply bridging oxygen atom, and twelve carboxylic acid residues arranged in bidentate configuration along the edges of the octahedron. In addition, two unidentate oxygen atoms, believed to be in hydroxyl groups, are attached to two opposite cerium atoms of the $Ce_6$ octahedron. From the infrared spectra obtained by IR-analysis of solutions of the novel cerium (IV) oxidic compounds, this structure is largely conserved in the organic solvent solutions and in the liquid cerium (IV) carboxylates.

Preferred such compounds may be represented by the formula:

$$H_6Ce_6O_8(OH)_2(RCOO)_{12}$$

in which R is an alkyl radical having from 3 to 9 carbon atoms, having an octahedral structure with the six cerium atoms at the apexes of the octahedron, the twelve carboxylate residues forming bidentate bridges between the cerium atoms along the edges of the octahedron, one triply bridging oxygen atom on each face of the octahedron and two unidentate hydroxyl ligands completing the coordination of two opposing cerium atoms.

According to the present invention, the novel cerium (IV) oxidic compounds are prepared by mixing, preferably in an aqueous reaction medium, a cerium (IV) salt with a salt of an organic oxyacid advantageously having a pKa greater than 1, or with a mixture of salts of organic oxyacids, at least one of which advantageously having a pKa greater than 1 (which may be formed in situ) employing at least two molecular proportions of said salt of an organic oxyacid per atom of cerium.

The organic oxyacid salt is preferably prepared by reacting the organic oxyacid with an alkali metal, alkaline earth metal or ammonium (preferably tetra(lower alkyl) ammonium) oxide, hydroxide, carbonate or hydrogen carbonate (bicarbonate) immediately prior to use, or is prepared, in situ, in the presence of the cerium (IV) salt.

It has been determined that it is highly preferable to employ at least four molecular proportions of the organic oxyacid salt per atom of cerium to attain complete reaction. It is believed that this is because the initial product of the reaction is an intermediate containing four acid residues per cerium atom. This intermediate then hydrolyzes to produce the compounds in accordance with the present invention having, for each cerium atom, an oxygen atom and two oxyacid residues, together with associated hydroxyl or water ligands.

The cerium (IV) salt is preferably water soluble and may be, for example, a nitrate or sulfate. Preferably, it is ceric ammonium nitrate. The cerium (IV) salt may also be reacted with the salt of the organic oxyacid in an organic solvent, especially a highly polar organic solvent.

It is also possible to use basic cerium (IV) compounds in suspension, e.g., cerium (IV) carbonate, cerium (IV) oxycarbonate, or cerium (IV) hydroxycarbonate. Such basic cerium (IV) compounds may be reacted with four moles of organic oxyacid per mole of cerium, in the absence of any additional added base.

The salt of the organic oxyacid is preferably an alkali metal salt, such as a sodium or potassium salt, or an ammonium salt.

The reaction may be carried out at any temperature ranging from 0° C. to the boiling point of the reaction mixture, e.g., ranging from 10° to 80° C., but is preferably carried out ambient temperature, e.g., 20° C. up to 30° C.

The salt of the organic oxyacid is preferably prepared in situ by reacting the acid with an alkali metal, alkaline earth metal, or ammonium oxide, hydroxide, hydrogen carbonate or carbonate, e.g., sodium hydroxide or ammonium hydrogen carbonate, to a pH in the range of 7 to 10, preferably about 8.

When an aqueous reaction medium is used, the concentration of the cerium (IV) salt conveniently ranges from 0.1 to 2.0 molar. This solution may be added to the preformed solution of the organic oxyacid salt in a concentration which is preferably 0.5 to 2 molar.

The oxyacids used in the present invention are characteristically organic oxyacids having a pKa greater than 1, and typically greater than 2, preferably carboxylic acids containing at least 2 carbon atoms, and typically alkanoic acids having 4 to 20, preferably 4 to 12, carbon atoms, which may either be linear or branched chain. Dicarboxylic acids having 4 to 12 carbon atoms, or aromatic or arylaliphatic acids such as benzoic acid, which may be substituted by alkyl radical substituents having up to 12 carbon atoms, can also be used. These acids may be used individually or in admixture.

While increasing the number of carbon atoms increases the solubility of the cerium (IV) oxidic compounds in hydrocarbon solvents, it also reduces the concentration of cerium values in the solution. It is therefore advantageous that the average number of carbon atoms present in the oxyacid or mixture of oxyacids should preferably range from 3 to 15 and more preferably from 4 to 8.

Exemplary oxyacids which are suitable according to the present invention include acetic acid, propionic acid, butyric acid, isobutyric acid (2-methylpropionic acid), pivalic acid, 2-methylbutyric acid, 2,2-dimethylbutyric acid, 2-ethylbutyric acid, 2-methylpentanoic acid, 2-ethylhexanoic acid (octanoic or octoic acid), ethylacetoacetic acid, 3,5-dimethylhexanoic acid, cyclohexane carboxylic acid, neohexanoic acid (2,2-dimethylbutyric acid), neoheptanoic acid (2,2-dimethylpentanoic acid), neooctanoic acid, isononanic acid (cekanoic acid), neodecanoic acid, undecylenic acid, perfluorobutyric acid, benzoic acid, p-tert-butylbenzoic acid, naphthenic acid, anthranilic acid, behenic acid, maleic acid, sebacic acid, bis(2-ethylhexyl) phosphoric acid, dodecylbenzene sulfonic acid, dodecylsulfuric acid, p-toluene sulfonic acid and mixtures thereof.

The oxyacids may either be straight or branched chain. Carboxylic acids substituted in the alpha- or beta- position relative to the carboxylic acid function often form cerium (IV) derivatives having an advantageous degree of solubility, especially when they bear only a single substituent, and preferably when they contain not more than four carbon atoms.

The oxyacids should be selected such as to be stable in the reaction medium employed to synthesize the novel compounds of the invention. The organic oxyacids may be substituted, e.g., by halogen atoms, or hydroxyl or oxo groups, as in pyruvic acid, alpha-hydroxy carboxylic acids, and keto acids such as acetoacetic acid. They may also contain ether or ester groups. Since cerium (IV) is a strong oxidizing agent, it is advisable to avoid the use of carboxylic acids which are readily oxidized, e.g., because they contain plural double bonds or other oxidizable groups.

The cerium (IV) oxidic compounds of the present invention are surprisingly soluble in apolar solvents, e.g., hydrocarbons, but also in polar solvents, e.g., carboxylic acids, ethers, alcohols and halogenated hydrocarbons. The preferred cerium (IV) oxidic compounds for dissolution, or dilution, in hydrocarbons are those in which n ranges from 0 to 2 and/or the total number of carbon atoms in the radicals A is at least 10, and preferably at least 24, per atom of cerium. For liquid formulations of high cerium content, the total number of carbons per atom of cerium should not exceed 60. The structure of the carboxylate ligand is considered important in determining the stoichiometry and organosolubility of the ceric carboxylate compound. The results obtained for homoleptic (single ligand) complexes are reported in Table I below:

TABLE 1

| CARBOXYLATE CHAIN STRUCTURE | MINIMUM CARBON ATOM CONTENT OF OXYACID FOR PRODUCT TO BE: | |
| --- | --- | --- |
| | A. HYDROCARBON MISCIBLE LIQUID | B. HYDROCARBON SOLUBLE SOLID |
| 2-Methyl branched | $C_6$ | $C_5$ |
| 2-Ethyl branched | $C_8$ | $C_6$ |
| 2,2-Dimethyl branched | $C_{10}$ | $C_6, C_7$ |
| Chain branched | $C_8$ | |
| Linear | | $>C_{10}$ |

Exemplary, specific cerium (IV) oxidic compounds include:

Cerium (IV) oxidic acetate octoate$^L$,
Cerium (IV) oxidic anthranilate octoate,
Cerium (IV) oxidic dibehenate,
Cerium (IV) oxidic dibenzoate,
Cerium (IV) oxidic benzoate octoate,
Cerium (IV) oxidic bis(2-ethylhexyl)phosphate$^L$,
Cerium (IV) oxidic bis(2-ethylhexyl)phosphate octoate$^L$,
Cerium (IV) oxidic dibutyrate,
Cerium (IV) oxidic butyrate octoate$^L$,
Cerium (IV) oxidic dicekanoate$^L$,
Cerium (IV) oxidic di(cyclohexane carboxylate$^L$),
Cerium (IV) oxidic di(2,2-dimethylbutyrate),
Cerium (IV) oxidic didodecylsulfate,
Cerium (IV) oxidic dodecylsulfate octoate,
Cerium (IV) oxidic didodecylbenzenesulfonate,
Cerium (IV) oxidic dodecylbenzenesulfonate octoate$^L$,
Cerium (IV) oxidic di(2-ethylbutyrate$^S$),
Cerium (IV) oxidic 2-ethylbutyrate octoate$^L$,
Cerium (IV) oxidic diisobutyrate,
Cerium (IV) oxidic isobutyrate octoate$^L$,
Cerium (IV) oxidic isobutyrate$_{3.0}$octoate$_{1.0}$$^S$,
Cerium (IV) oxidic dimaleate,
Cerium (IV) oxidic maleate octoate,
Cerium (IV) oxidic di(2-methylbutyrate$^S$),
Cerium (IV) oxidic 2-methylbutyrate octoate$^L$,
Cerium (IV) oxidic di(2-methylpentanoate$^L$),
Cerium (IV) oxidic dinaphthenate$^L$,
Cerium (IV) oxidic dineodecanoate$^L$,
Cerium (IV) oxidic dineoheptanoate$^S$,
Cerium (IV) oxidic dineooctanoate$^L$,
Cerium (IV) oxidic dioctoate$^L$,
Cerium (IV) oxidic (octoate)$_3$(EAA)$^L$,
Cerium (IV) oxidic perfluorobutyrate,
Cerium (IV) oxidic dipivalate,
Cerium (IV) oxidic pivalate octoate$^L$,
Cerium (IV) oxidic dipropionate,
Cerium (IV) oxidic propionate octoate$^S$,
Cerium (IV) oxidic di-p-tertbutylbenzoate$^S$,
Cerium (IV) oxidic p-tertbutylbenzoate octoate$^L$,
Cerium (IV) oxidic p-toluenesulfonate octoate,
Cerium (IV) oxidic disebacate,
Cerium (IV) oxidic sebacate octoate,
Cerium (IV) oxidic diundecylenate$^S$,
Cerium (IV) oxidic undecylenate octoate$^L$, wherein L connotes a hydrogen soluble liquid, S connotes a hydrocarbon soluble solid and EAA connotes ethylacetoacetate.

The novel cerium (IV) oxidic compounds of this invention may be used in solution, or as neat liquids, especially in film-forming compositions which dry via atmospheric oxidation, e.g., in paints. They may also be used to promote combustion of hydrocarbon fuels, in particular diesel fuels. For these purposes, they may be dissolved in suitable solvents at the time of use, but it is a significant advantage of the novel cerium (IV) oxidic compounds that they can easily be formulated and stored as concentrated liquids having a high cerium (IV) content, e.g., greater than 10% and preferably greater than 20% or even 30% of the total weight thereof. Such liquids are characterized, inter alia, by having, for a given Ce(IV) content, a lower viscosity than Ce(IV)-containing liquids previously known to this art. More particularly, a Ce(IV) liquid in accordance with the present invention containing 20% Ce(IV) typically has a viscosity at 20° C. of less than 1 poise, e.g., 0.5 to 1 poise. Such liquid cerium (IV) oxidic compounds in accordance with the present invention are easily blended into hydrocarbons, or compositions based on hydrocarbon solvents (e.g., film-forming compositions), with which they are generally miscible and generally in all proportions. They are especially useful as combustion-promoting additives in hydrocarbon fuels, including fuels for internal combustion, especially diesel, engines.

The novel cerium (IV) oxidic compounds of the present invention may also be introduced into the filters or soot traps (reservoirs) of vehicular exhaust lines, these being designed to trap the carbon-containing particles produced by combustion of the various combustible materials or fuels, notably diesel fuels (compare U.S. Pat. No. 4,621,593 and Lemaire et al copending application Ser. No. 08/156,649 [Attorney Docket No. 022701-447], filed Nov. 24, 1993, now abandoned, and assigned to the assignee hereof.

In order to further illustrate the present invention and the advantages thereof, the following specific examples are given, it being understood that same are intended only as illustrative and in nowise limitative.

In said examples to follow, the oxyacid or mixture of oxyacids (4.0 mol proportions) was converted into its alkali metal, alkaline earth metal or ammonium salt by reacting same with the stoichiometric amount of an appropriate oxide, hydroxide, hydrogen carbonate or carbonate, preferably a hydrogen carbonate, and preferably ammonium hydrogen carbonate. The salt thus formed was added to an aqueous solution of a cerium (IV) salt, preferably ceric ammonium nitrate (1.0 mol proportions) at ambient temperature with stirring. The desired final product separated out as a solid or liquid. If it formed a solid, it was filtered off. If it formed a liquid, it was extracted with a hydrocarbon solvent and the organic solution obtained was then separated and washed with water. The washed organic solvent solution was then evaporated, e.g., in a rotary evaporator, to remove the organic solvent. During the evaporation, hexane or other suitable solvent was added to remove any residual water by azeotropic distillation. The solvent-free product was then obtained as a liquid.

In an alternative preferred embodiment, the solid inorganic base was directly added to a stirred two-phase system containing the organic oxyacid and the aqueous ceric ammonium nitrate solution, in a one-pot reaction. The organic salt of the oxyacid was formed, in situ, and reacted with the aqueous ceric ammonium nitrate solution to provide the desired cerium (IV) organic compound. Any intermediate cerium (IV) species containing carbonate formed by side reaction of the inorganic base with the aqueous cerium (IV) solution themselves react with the remaining organic oxyacid to yield the same cerium (IV) organic compound.

This process could also be carried out in the complete absence of added organic or aqueous reaction medium, but it was highly preferable to dissolve the solid ceric ammonium nitrate, at least partially, before admixture with the organic oxyacid and subsequent reaction with the inorganic base, especially when the latter was added as a solid.

In Examples 1–22 below the oxyacid or mixture of oxyacids (0.4 mol) was first converted into its sodium salt via reaction with the stoichiometric amount of sodium hydroxide. The solution was then adjusted with 300 g $H_2O$. This was added to a solution of ceric ammonium nitrate (0.1 mol) in water (400 g) at ambient temperature, while the mixture was stirred. The desired product separated out as a solid or liquid and was processed in the manner described above.

The following Table II reports the oxyacids used, the yield of the cerium (IV) oxidic compound obtained and its form and cerium content:

TABLE II

| Example | Acid(s) (molar ratio) | Yield % | Form of Product | Cerium Content wt % | Comments |
|---|---|---|---|---|---|
| 1 | Butyric acid | 77.5 | Pale yellow solid | | Soluble iin 2-ethylhexanoic acid. |
| 2 | 2-Methylbutyric acid | 84 | Bright yellow crystals | 35.6 | Structure $H_6Ce_6(\mu_3\text{-}O)_8(OH)_2$ (eta, $\mu\text{-}RCO_2)_{12}$ (eta, $\mu RCO_2)_{12}$ with a $Ce_6$ octahedron, 8 × face-bridging O, 12 × bidentate edge-bridging $RCO_2$, confirmed by X-ray crystallography. All hydrogen atoms not located. |
| 3 | Pivalic acid | 97.5 | Page yellow solid | 33.8 | Soluble in hydrocarbons in the presence of 2 equivalents of octanoic acid |
| 4 | 2-ethylhexanoic acid | >95 | Yellow oil | 19.0 | Hydrocarbon miscible, considered to be $[CeO(RCOO)_2.2RCOOH]_6$ |
| 5 | Acetic acid/2-ethylhexanoic acid (1:1) | 76 | Thick yellow oil containing crystals | 25.5 | |
| 6 | Propionic acid/2-ethylhexanoic acid (1:1) | 81.4 | Very sticky dark yellow solid | 27.6 | Hydrocarbon soluble |
| 7 | 2-ethylhexanoic acid/ethylaceto acetate (1:1) | 70 | Cloudy yellow oil | 18 | |
| 8 | 2-Methylbutyric acid/2-ethylhexanoic acid (1:1) | 98.5 | Slightly hazy amber oil | 21.4 | Hydrocarbon soluble, consider to be $[CeO(2\text{-methylbutyrate})_2, (2\text{-Ethylhexanoic acid})_2]_6$ |
| 9 | Pivalic acid/2-ethylhexanoic acid (1:1) | 96 | Hazy amber liquid | 22.5 | Forms stable solution in 2-ethylhexanol at 10% Ce |
| 10 | Undecylenic acid/2-ethylhexanoic acid (1:1) | 93.4 | Clear yellow oil | 15.9 | |

| Example | Acid(s) (molar ratio) (Acid:Acid) | Yield % | Form of Product | Cerium Content wt % | Comments |
|---|---|---|---|---|---|
| 11 | Maleic acid/2-ethylhexanoic acid (1:2) | 89 | Sticky yellow powder | 28.0 | |
| 12 | Dodecylsulfuric acid/2-ethylhexanoic acid (1:1) | 22.9 | Bright yellow cloudy liquid | 18.9 | |
| 13 | 3,5-Dimethylhexanoic acid | 98 | Cloudy orange oil | 21.2 | |
| 14 | Neodecanoic acid | 91 | Viscous orange oil | 16.3 | |
| 15 | Undecylenic acid | 85 | Opaque yellow waxy solid | 12.7 | Liquifies at 50° C. |
| 16 | Maleic acid | 88 | Yellow powder | 35.8 | |
| 17 | Sebacic acid/2-ethylhexanoic acid (1:2) | 76 | Light yellow soft waxy solid | 17.4 | |
| 18 | Sebacic acid | 90 | Yellow powder | 23.0 | % Ce determined by firing |
| 19 | Benzoic acid | 43 | Pale yellow crystals | 28.9 | |
| 20 | Benzoic acid/2-ethylehxanoic acid (1:1) | 96.6 | Very thick dark orange liquid | 20.1 | Crystallizes after 2 days |
| 21 | Tert-butylbenzoic acid | 83 | Yellow crystalline solid | 17.5 | |

EXAMPLE 23

The large scale production of a cerium (IV) oxidic compound of the invention was carried out as follows: Ceric ammonium nitrate (100 parts by weight, one mole equivalent) was partially dissolved in water (45.45 parts by weight) with stirring. The dissolution was endothermic and an orange solution was obtained. 2-Ethylhexanoic acid (104.72 parts by weight, 4 mole equivalents) was added with rapid stirring. The temperature of the mixture was adjusted to 40° C. and solid ammonium bicarbonate (57.46 parts by weight, 4 mole equivalents) was then added in portions (each about 5 parts by weight) over a period of time of 30 minutes. Carbon dioxide was evolved and a yellow oily product formed.

The reaction mixture was maintained at about 40° C. with continued stirring for one additional hour, and then permitted to cool to ambient temperature without stirring. Most of the desired final product separated out as a clear, yellow upper organic layer.

Heptane (63.63 parts by weight) was then added with stirring to dissolve the separated product and extract residual product from the aqueous phase. The lower aqueous layer was then removed. The organic layer was washed with water (90 parts by weight) and again separated. The heptane was removed from the organic layer by vacuum distillation at 45° C.–50° C. (<50 mm Hg). Any remaining water was removed by distillation with the heptane. The residue was the desired product. It formed a clear bright yellow oil containing 19.0 to 19.5% w/w Ce, of which >95% was Ce(IV), and which had a viscosity of about 0.9 poise. The product contained >99% of the cerium initially used.

Infrared and Raman Spectroscopy

The various compounds all shared the same major infrared absorbances, reported in Table III below:

TABLE III

| BAND | | ASSIGNMENT |
| --- | --- | --- |
| 1. 3,650 cm$^{-1}$ | strong, very sharp | υ OH? υ Ce—O—H? or isolated OH of carboxylic acid |
| 2. 3,400–2,400 cm$^{-1}$ | strong, very broad | υ OH of free carboxylic acid |
| 3. 1,750–1,720 cm$^{-1}$ | very strong very sharp | υ C = O of carboxylic acid |
| 4. 1,580–1,550 cm$^{-1}$ | very strong very sharp | υ C = O of μ, η carboxylate |
| 5. 700–500 cm$^{-1}$ | weak, complex | υ Ce-0 of cluster framework |

Comparison of bands 2 and 3 with those of the relevant free acids evidences them to be identical. The similarity of the infrared spectra for all of the solid Ce$^{IV}$ carboxylates vis-a-vis that of Ce$^{IV}$ 2-methylbutyrate suggests that they are isostructural, all containing the Ce$_6$ nucleus. The variation in intensity of bands 2 and 3 relative to 4 correlates with the higher than theoretical acid to metal ratio determined for these complexes, often nearer 2.5:1 than 2:1.

Figure 2:
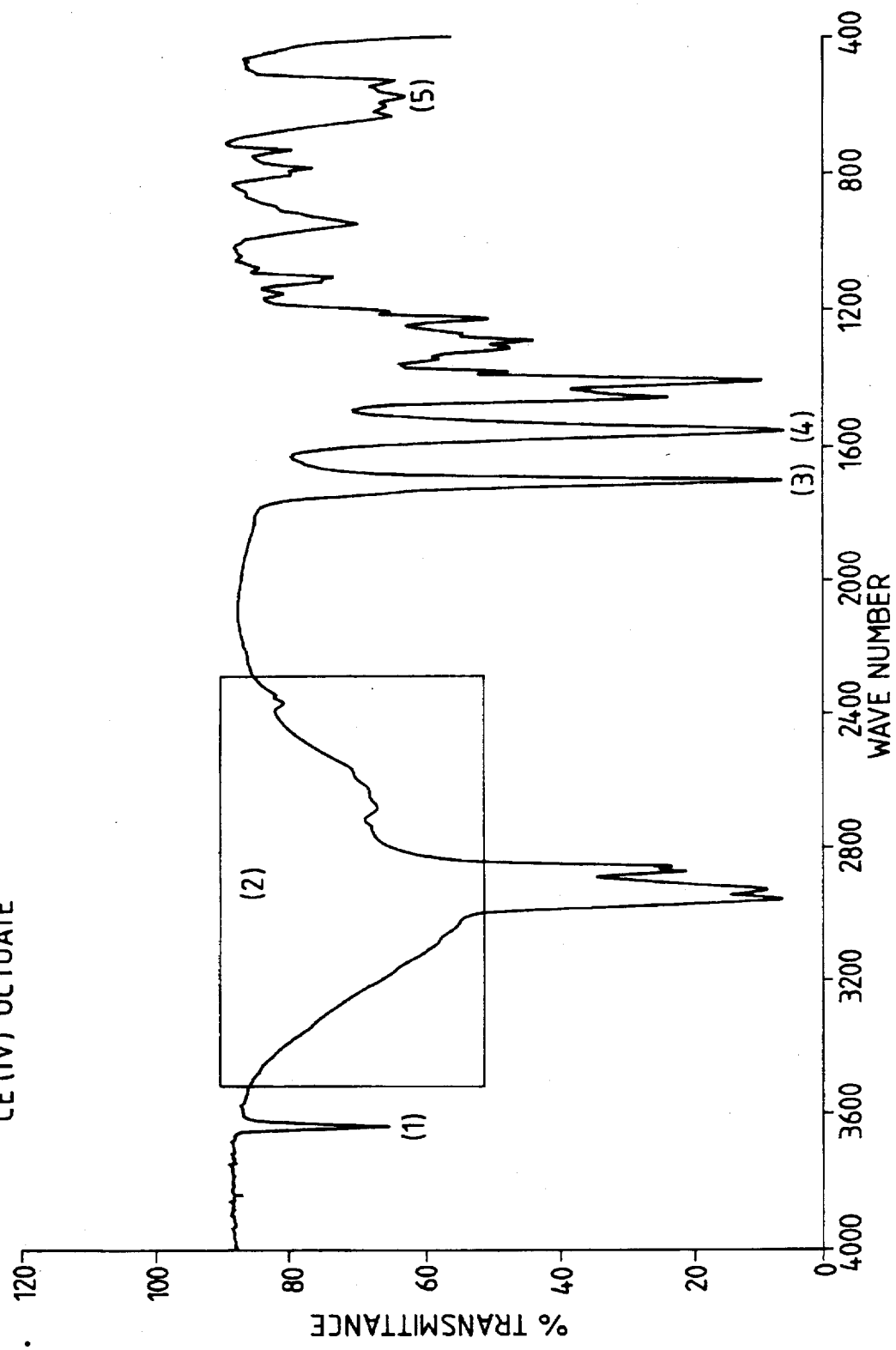
Figure 3:
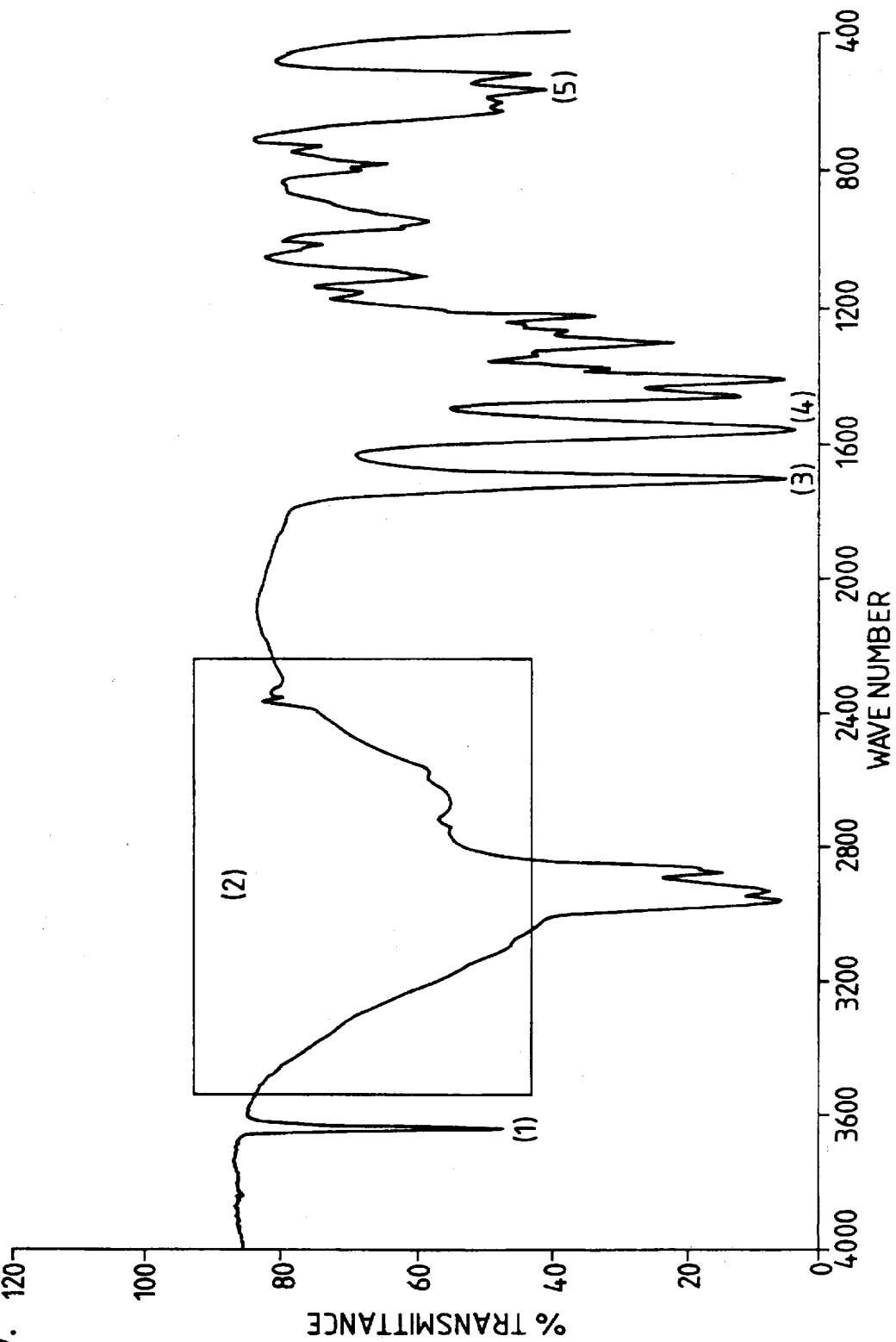

In the accompanying Figures of Drawing, FIGS. 1, 2 and 3 respectively illustrate the infrared absorption spectra of the products of Examples 2 (2-methylbutyrate), 4 (2-ethylhexanoate, i.e., octoate), and 8 (mixed 2-methylbutyrate/octoate). In these spectra, the characteristic absorption bands (1) to (5) noted in the above Table have been indicated.

Figure 5:
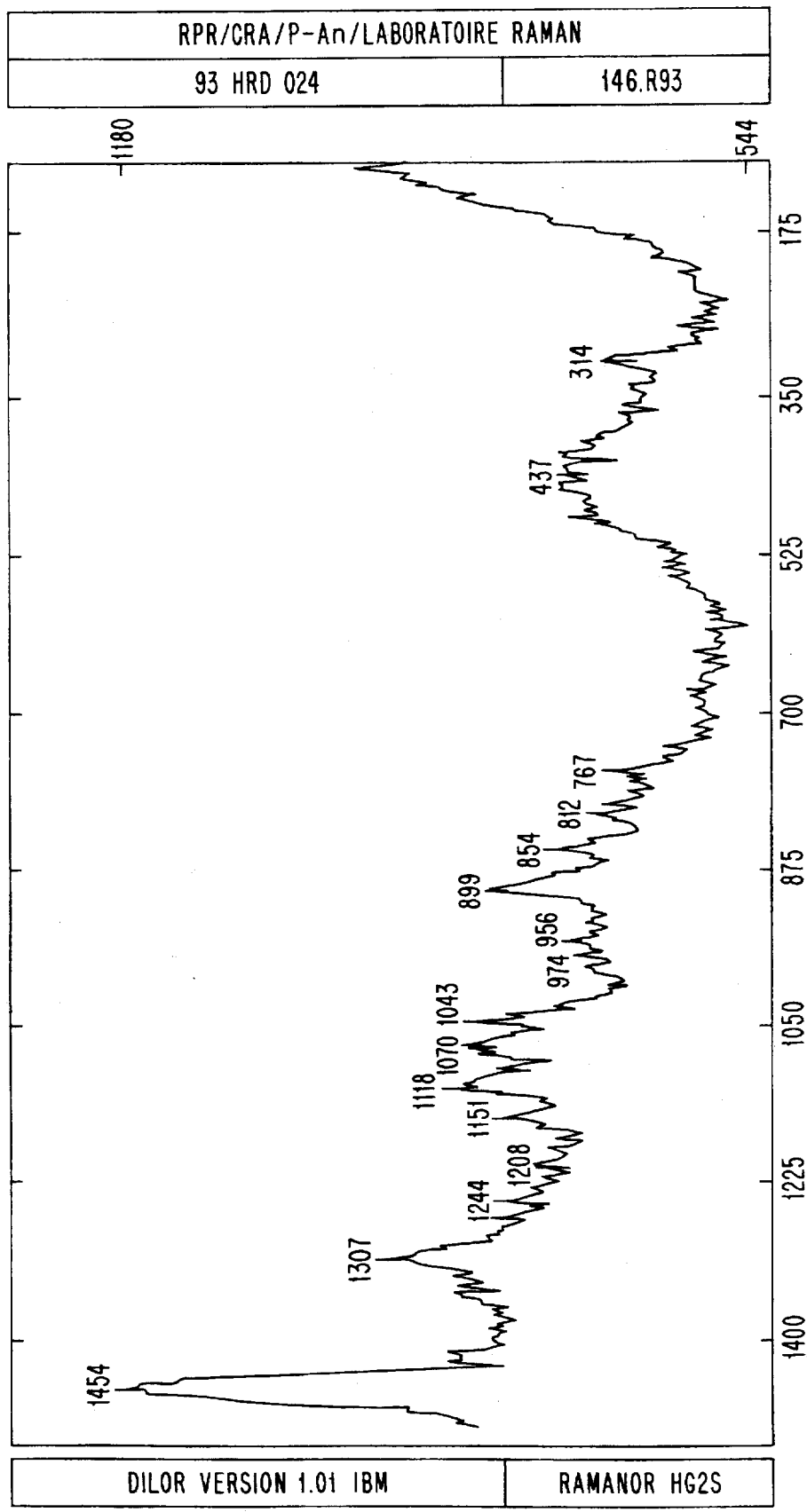
FIGS. 5 and 6 are Raman spectra of compounds prepared according to U.S. Pat. No. 4,599,201/EP-A-0,093,627.
Figure 6:
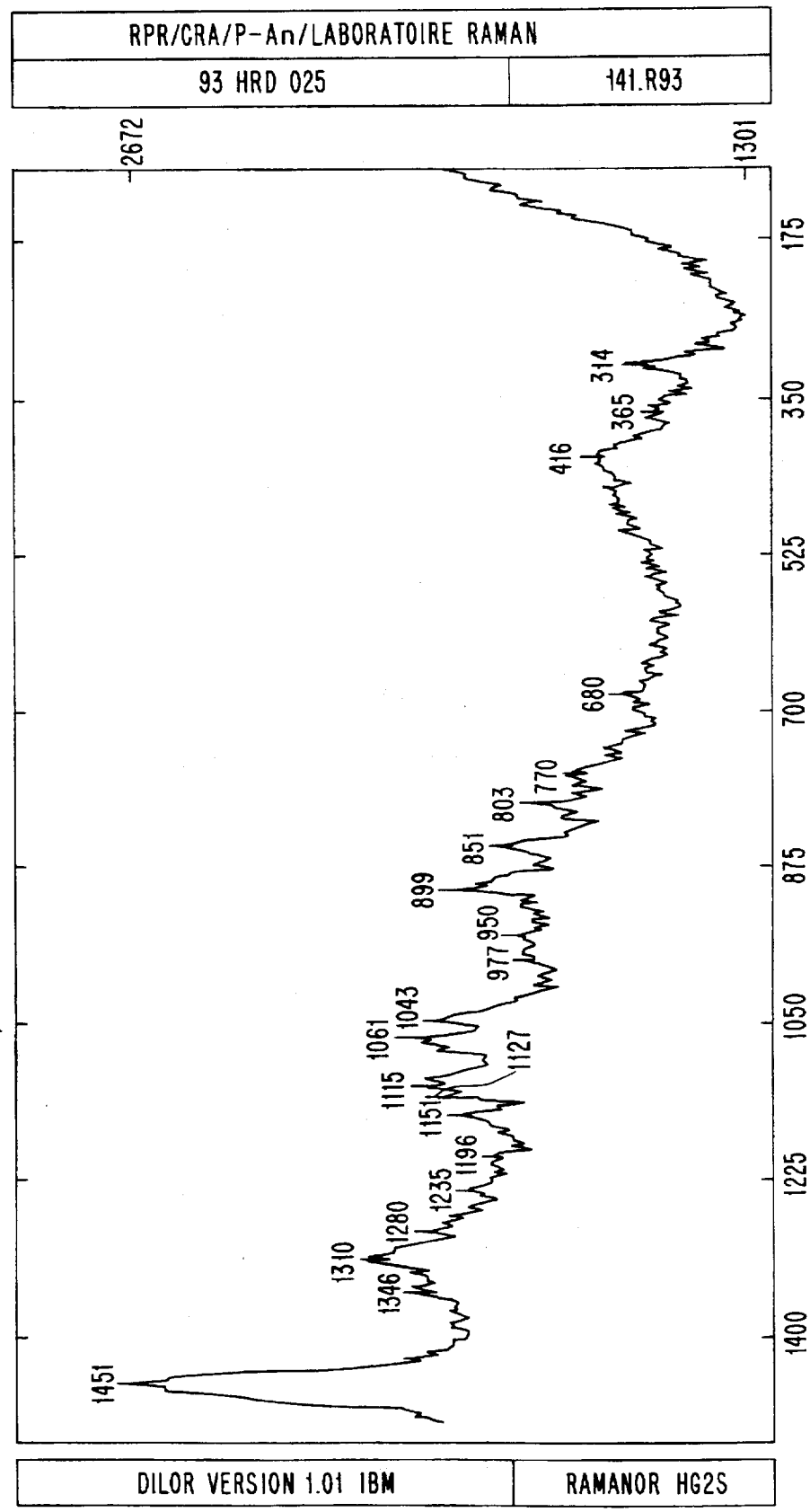
Figure 7:
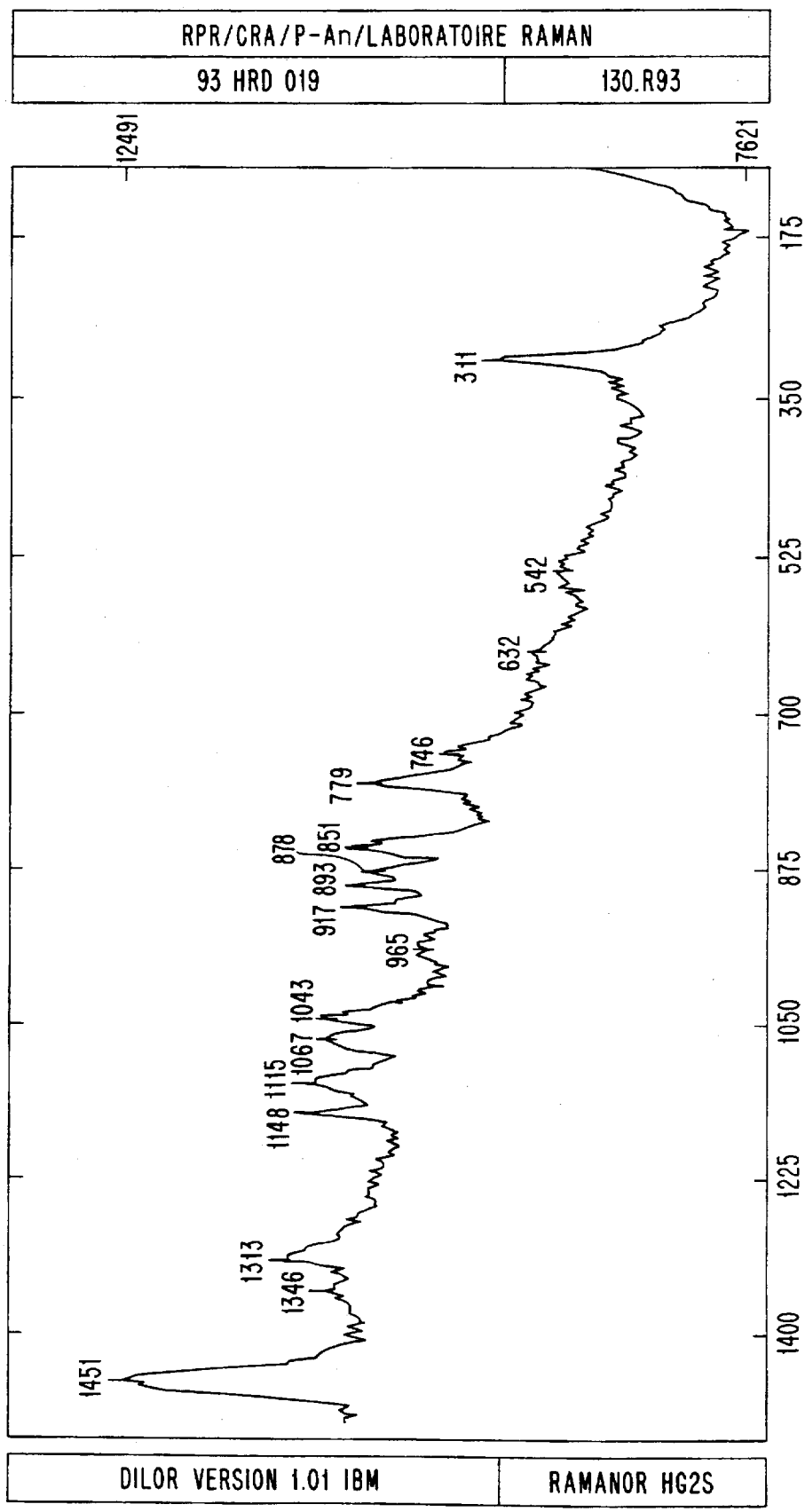
FIG. 7 is a Raman spectrum of octoic acid, per se.

Also in the accompanying Figures of Drawing, FIGS. 4, 5, 6 and 7 respectively illustrate the Raman spectra of the cerium (IV) oxidic octoate (viscosity=2.0 poise; 19.2% Ce; 96.5% Ce(IV)/total Ce) prepared according to this Example 23 (FIG. 4), the cerium octoate (viscosity=65 poise; 20.9% Ce; 65.7% Ce(IV)/total Ce) prepared according to Example 7 of U.S. Pat. No. 4,599,201/EP-A-0,093,627 (single treatment with H$_2$O$_2$)(FIG. 5), the cerium octoate (viscosity= 16.5 poise; 19.3% Ce; 68.6% Ce(IV)/total Ce) prepared according to Example 4 of U.S. Pat. No. 4,599,201/EP-A-0,093,627 (dual treatment with H$_2$O$_2$) (FIG. 6), and octoic acid itself (FIG. 7). By "octoate" and "octoic" are intended, respectively, 2-ethylhexanoate and 2-ethylhexanoic. Each of the samples was a relatively viscous yellowish liquid, and the samples of FIGS. 5 and 6 were not totally pure.

These Raman spectra conspicuously delineate the cerium (IV) oxidic octoate according to the invention from the cerium octoate prepared according to the Gradeff et al process described in U.S. Pat. No. 4,599,201/EP-A-0,093,627.

Raman diffusion refers to vibrational spectroscopy carried out by inelastic light scattering. For this purpose, a Raman Jobin-Yvon spectrometer was used, model Raman or HGS2 (Djilor computerized). The ionized argon laser operated via the green line at 514.5 nm. Other experimental conditions are reported on the spectra of FIGS. 4–7.

The liquids analyzed were contained in a glass tube (for NMR). Laser power in the tubes was approximately 100 mW.

Figure 4:
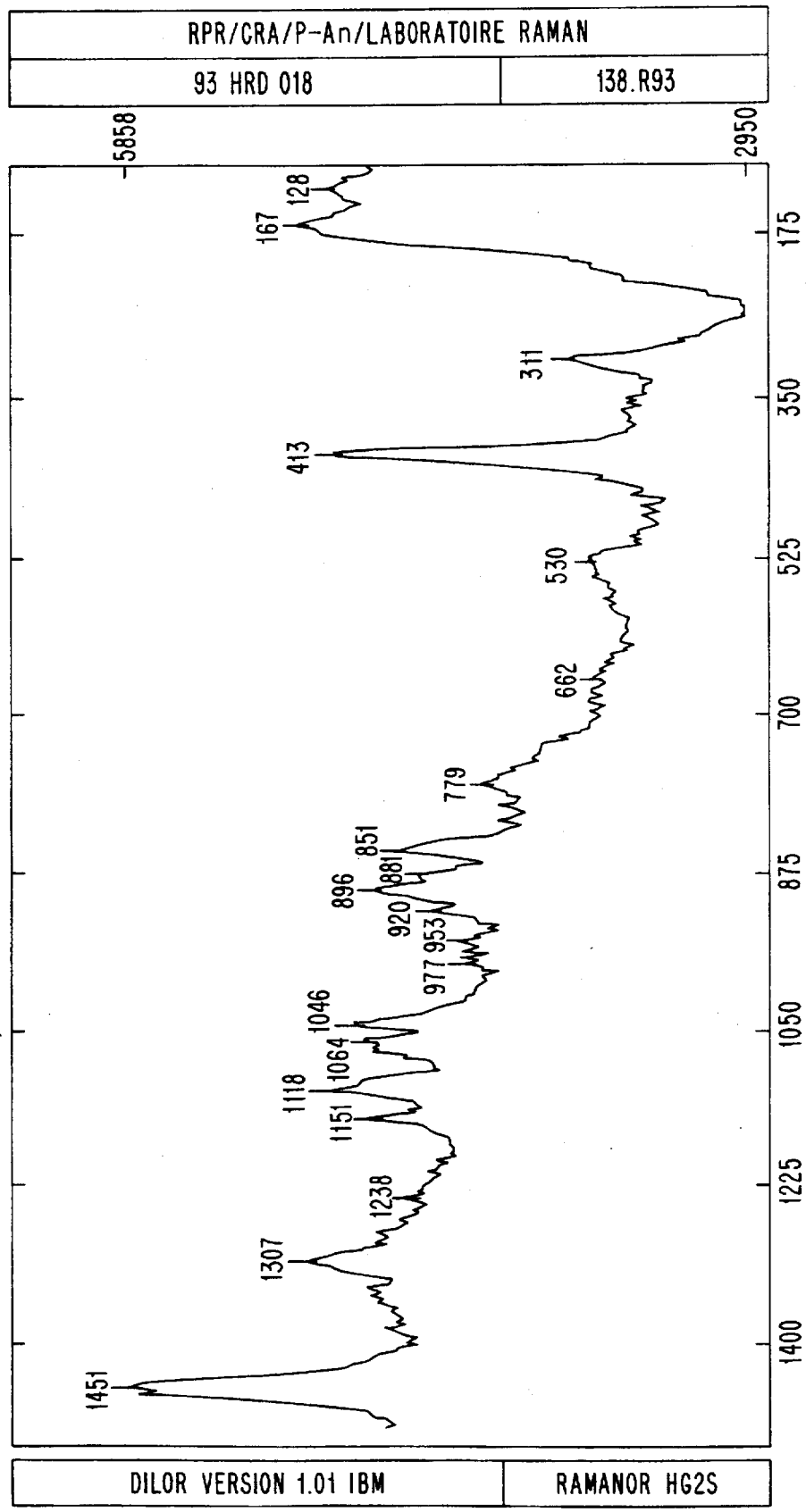
FIG. 4 is a Raman spectrum of the compound of Example 23 according to this invention.

Thus, the spectra of FIG. 4 (cerium (IV) oxidic octoate) and FIG. 7 (octoic acid) were compared. The lines resulting from chelation at 413, 167 and 128 cm$^{-1}$ were then clearly evidenced. The first, at 413 cm$^{-1}$, corresponded to a valence mode (Ce-0), and the two others to angle-deformation modes.

The spectra of FIG. 4 (compound according to the invention) and FIG. 5 and FIG. 6 (single and dual treatment with H$_2$O$_2$) were also compared. That of FIG. 4 had a clearly defined line at 413 cm$^{-1}$. This line did not exist in the case of the compounds of FIGS. 5 and 6. Moreover, the spectrum of FIG. 4 reflects a single line at 779 cm$^{-1}$; those of FIGS. 5 and 6 reflect a doubling thereof (810, 770 cm$^{-1}$).

With respect to the number of H$_2$O$_2$ treatments per Gradeff et al, the Raman spectra of FIGS. 5 and 6 are quite similar. In both cases, however, these spectra differ markedly from the spectrum of FIG. 4.

On final analysis, the presence (FIG. 4) or absence (FIGS. 5 and 6) of a thin line at about 413 cm$^{-1}$ clearly exposed the chemical difference (nature of the Ce—O bonds) between the two types of compounds. Raman spectroscopy is thus a very effective technique for comparison, supplementing infrared. While the line at 413 cm$^{-1}$ via Raman probably exists in the far infrared, the latter is not a common laboratory technique, since the sample must be packed in a polyethylene vessel of determinate thickness.

Ultraviolet Spectroscopy

All of the final Ce$^{IV}$ carboxylates were yellow or orange in color. However, the UV absorptions promoting this color were weak and masked beneath the strong metal carboxylate absorbances below 350 nm.

Ce$^{IV}$ 2-methylbutyrate gave a weak shoulder to this feature with $\lambda_{max}$=350 nm and $\epsilon$=212.

EXAMPLE 24

2-Ethylhexanoic acid (922.88 g, 6.4 mol) was placed in a reaction vessel and water (3 liters) was added. Sodium hydroxide solution (50%, 512 g, 6.4 mol) was then added rapidly through a dropping funnel. The temperature of the mixture increased to 49° C. and the mixture was then further heated to 80° C. The mixture was stirred for 30 minutes until it became clear. The pH was measured with a pH meter and if it was above 8.5, additional 2-ethylhexanoic acid was added to adjust the pH to about 8.5. Ceric ammonium nitrate (904.36 g, 1.6 mol) was dissolved in water (2 liters) and the solution was added to the heated solution of sodium 2-ethylhexanoate through a dropping funnel over a period of one-half hour. A solid sticky material precipitated at first, but it dissolved later. The mixture was cooled to ambient temperature and hexane (600 g or more if required) was added to extract the product. The organic layer was separated and washed with water 2 to 4 times (400 ml water each time) until the wash water contained no detectable nitrate. If desired, at this stage the aqueous layer from the reaction mixture and the aqueous washes can be combined and back-extracted with more hexane (100 ml), in which case the hexane extract was washed with water to remove nitrate and combined with the principal hexane extract.

The hexane solution of the desired product was then filtered, if cloudy, and hexane was removed by distillation in vacuo at ambient or slightly elevated temperature (below 50° C.). The product was an orange oil having a density of 1.2 g/ml and a viscosity of 281 cps. The yield was 1120 g (92.2%), without back-extraction of the aqueous layer. The product had a cerium content of 18.46%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a cerium (IV) oxidic compound comprising reacting a cerium (IV) salt with a salt of an organic oxyacid, or with an admixture of salts of organic oxyacids to produce a cerium (IV) oxidic compound having each Ce (IV) atom being coordinated with two anions of said salt of an organic oxyacid, or said admixture of salts of organic oxyacids, and at least one additional oxygen atom which is not an oxygen atom in the salt of an organic oxyacid or in the admixture of salts of organic oxyacids.

2. The process as defined by claim 1, carried out in a liquid reaction medium employing at least two molecular proportions of organic oxyacid salt per atom of cerium.

3. The process as defined by claim 2, carried out in an aqueous reaction medium.

4. The process as defined by claim 1, said cerium (IV) salt comprising a nitrate or sulfate.

5. The process as defined by claim 4, said cerium (IV) salt comprising ceric ammonium nitrate.

6. The process as defined by claim 1, said organic oxyacid salt comprising an alkali or alkaline earth metal, or ammonium salt.

7. The process as defined by claim 2, carried out in a liquid reaction medium employing at least four molecular proportions of organic oxyacid salt per atom of cerium.

8. The process as defined by claim 1, comprising preparing said organic oxyacid in situ, in the presence of said cerium (IV) salt.

9. The process as defined by claim 3, the concentration of said cerium (IV) salt in said aqueous reaction medium ranging from 0.1 to 2.0 molar.

10. The process as defined by claim 9, comprising adding a 0.5 to 2 molar solution of said organic oxyacid salt to said aqueous reaction medium.

11. The process as defined by claim 1, said organic oxyacids having a pKa greater than 1.

12. The process as defined by claim 11, said organic oxyacids having a pKa greater than 2.

13. The process as defined by claim 1, each of said organic oxyacids comprising a carboxylic, organosulfuric, organosulfonic, organophosphoric or organophosphonic acid.

14. The process as defined by claim 13, each of said organic oxyacids comprising a carboxylic acid.

* * * * *